(12) United States Patent
Schon et al.

(10) Patent No.: US 7,417,235 B2
(45) Date of Patent: Aug. 26, 2008

(54) PARTICLE DETECTOR FOR SECONDARY IONS AND DIRECT AND OR INDIRECT SECONDARY ELECTRONS

(75) Inventors: Armin Schon, Nes Ziona (IL); Eli Cheifetz, Ramat-Gan (IL); Semyon Shofman, Qiriat Ekron (IL)

(73) Assignee: El-Mul Technologies, Ltd., Soreq, Yavne (IL)

( * ) Notice: Subject to any disclaimer, the term of this patent is extended or adjusted under 35 U.S.C. 154(b) by 282 days.

(21) Appl. No.: 11/431,713

(22) Filed: May 11, 2006

(65) Prior Publication Data

US 2006/0289748 A1    Dec. 28, 2006

Related U.S. Application Data

(60) Provisional application No. 60/679,669, filed on May 11, 2005.

(51) Int. Cl.
*B01D 59/44* (2006.01)
*H01J 37/244* (2006.01)

(52) U.S. Cl. .............. 250/397; 250/399; 250/299; 250/370.11; 250/390.11; 250/207; 250/208.2; 250/227.11; 250/227.32; 250/570; 313/103 R; 313/103 CM; 313/105 CM; 313/104; 313/535; 313/532; 313/528; 313/527; 313/525

(58) Field of Classification Search .............. 250/207, 250/208.1, 208.2, 208.5, 208.6, 222.2, 227.11, 250/227.32, 361 R, 362, 367, 361 C, 370.11, 250/390.11, 472.1, 473.1, 570; 313/103 R, 313/103 CM, 104, 105 CM, 540, 542, 543, 313/535, 527–532, 525, 523

See application file for complete search history.

(56) References Cited

U.S. PATENT DOCUMENTS

| | | | | |
|---|---|---|---|---|
| 3,415,990 A | * | 12/1968 | Watson | 250/338.1 |
| 4,143,291 A | * | 3/1979 | Morales | 313/103 R |
| 4,680,468 A | * | 7/1987 | Bouchard et al. | 250/310 |
| 5,180,943 A | * | 1/1993 | Kyushima | 313/535 |
| 5,656,807 A | * | 8/1997 | Packard | 250/214 VT |
| 5,990,483 A | * | 11/1999 | Shariv et al. | 250/397 |
| 6,236,053 B1 | * | 5/2001 | Shariv | 250/397 |

(Continued)

FOREIGN PATENT DOCUMENTS

JP        62201385 A        9/1987

*Primary Examiner*—David A Vanore
*Assistant Examiner*—Bernard Souw
(74) *Attorney, Agent, or Firm*—Bacon & Thomas, PLLC

(57) ABSTRACT

A multi-purpose efficient charge particle detector that by switching bias voltages measures either secondary ions, or secondary electrons (SE) from a sample, or secondary electrons that originate from back scattered electrons (SE3), is described. The basic version of the detector structure and two stripped down versions enable its use for the following detection combinations: The major version is for measuring secondary ions, or secondary electrons from the sample, or secondary electrons due to back-scattered electrons that hit parts other than the sample together or without secondary electrons from the sample. Measuring secondary ions or secondary electrons from the sample (no SE3). Measuring secondary electrons from the sample and/or secondary electrons resulting from back-scattered electrons hitting objects other than the sample (no ions).

18 Claims, 8 Drawing Sheets

U.S. PATENT DOCUMENTS

| | | | |
|---|---|---|---|
| 6,730,907 B1 * | 5/2004 | Feuerbaum et al. | 250/310 |
| 6,750,455 B2 * | 6/2004 | Lo et al. | 250/346 |
| 6,940,066 B2 * | 9/2005 | Makarov et al. | 250/287 |
| 2004/0262531 A1 | 12/2004 | Gerlach et al. | |
| 2006/0231769 A1 * | 10/2006 | Stresau et al. | 250/397 |
| 2006/0289748 A1 * | 12/2006 | Schon et al. | 250/306 |

* cited by examiner

PARTICLE DETECTOR FOR SECONDARY IONS AND DIRECT AND OR INDIRECT SECONDARY ELECTRONS

FIELD OF THE INVENTION

The present invention relates to detecting secondary ions or secondary electrons produced by analytic or surface modification instruments such as Scanning Electron Microscopes (SEM), Focused Ion Beams (FIB), Scanning Auger instruments, Electron Beam Writing machines, etc. In these instruments surface properties in the form of images are obtained by measuring the current of secondary or reflected particles released or produced by a scanning particle beam.

BACKGROUND

Figure 1:
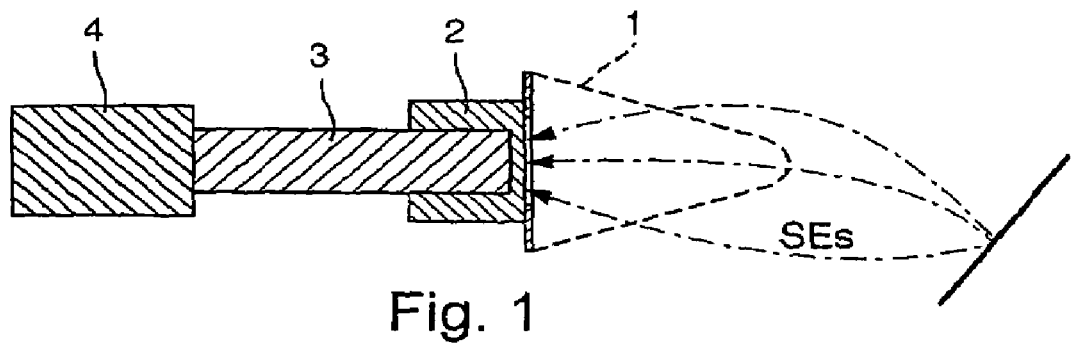

Almost all SEMs use an ETD (Everhardt Thornley Detector T. E. Everhart and R. F. M. Thornley "Wideband detector for microampere low-energy electron currents. J. Sci. Instr. 37, 246-248 (1960)) to measure the current of secondary electrons (SE) produced by the scanning of the electron beam on a sample. Relating the number of secondary electrons accumulated in a certain time bin to the location bombarded by the scanning beam at that time bin forms the image of the surface topography and properties that are reflected in variations of SE emission. A typical sketch of an ETD (prior art) is shown in FIG. 1. An electron collecting sparse electrode 1 at voltages +80 to +500 V attracts SE that are emitted from the sample at low energies of mostly few eV rarely reaching above 25 eV. The collected SE that pass the sparse grid are further accelerated to an aluminum coated scintillating plate 2 at +several kV to +15 kV that produce several hundred photons for each impinging accelerated electron. A light guide (LG) 3 attached to the back side of the scintillating plate guides tens % of the photons to a photomultiplier (PMT) 4. With a suitable design, the PMT of the ETD will start the signal multiplication with several photoelectrons (from the photocathode) for each electron accelerated to the scintillator. The collecting sparse grid and its voltage are designed to collect as large a number of SE as possible with minimal distortion of the impinging primary beam. This grid also shields the primary beam region from the electric field produced by the scintillating plate high voltage.

The collecting sparse grid in ETD produces a weak attracting electric field at the sample. It is quite efficient in collecting the low energy SEs provided there is no other attracting potential in the region of the sample and the grid line of sight to the sample is not hindered by physical obstacles. Its collection efficiency can reach from few tens % to 90%. However, the ETD is not a very effective for back scattered electrons (BSE), defined as electrons emitted from the sample at energies between 50 eV and the beam energy. Most of the BSE are emitted with energies from the beam energy to a third of the beam energy. Therefore the ETD collecting grid is inefficient in attracting these electrons and leading them to the scintillator. The BSE thus hit various parts and objects in the vacuum chamber and produced tretiery electrons that are denoted as SE3. Most of the SE3 are not collected by the ETD.

The ETD is also used in FIB and other ion bombarding schemes, to detect the SE induced by ion bombardment. In such a case there are also many low energy secondary positive ions as a result of sputtering and other processes. Detection of these ions gives additional information about the impinged surface. The positive ions can be attracted to the ETD and accelerated to the scintillator by reversing the voltages on the collecting grid and scintillating plate to negative values. The drawback of the ETD when used in this ion mode is very low or no efficiency for detecting secondary ions due to the very low luminosity response of any scintillator to impinging ions relative to same energy electrons, compounded by the ions high or total energy loss in the conducting aluminum layer of the scintillating plate.

A typical method to measure low energy positive ions (originating at energies 0 eV to 50 eV) is to accelerate them to a converter plate at voltage of −3 kV to −5 kV to produce SEs efficiently. One or more SE per impinging ion, for many types of atomic ions, are obtained for ion energies exceeding 3 keV. From the converting plate the few eV ion-induced SEs have to be accelerated to either an electron multiplying arrangement or to a scintillating layer at +5 kV to +15 kV relative to the converter plate. The scintillating layer is the scintillator of the ETD. Thus, response to low energy secondary ion current is obtained upon efficient transfer of the SE from the converter plate to the scintillator or to electron multiplying arrangement. Typical ion to electron converters are various forms of metallic plates with or without plating of SE enhancing materials, which are placed in the passage of the ions to the scintillator or to the electron multiplier.

The concept of a switchable electron and ion detector which can detect ions or electrons by just switching bias voltages on a converting plate or mesh is disclosed in a number of patent applications, i.e., Ishitani Toru, Hirose Hiroshi, and Onishi Takeshi, "Charged Particle Detector" (Japanese Patent Application no 64338358), Ishitani Tornu, Hirose Hiroshi, and Arima Yoshio, "Converging Ion Beam Device and Charged Particle Detector" (Japanese Patent Application 05295229), and R. L Gerlach, M. W. Utlaut, T. Dingle, and M. Uncovsky, "Particle detector Suitable for Detecting Ions and Electrons" (U.S. Patent Application 20040262531).

In the latter publication the converting surfaces are in the form of cylinders around the line connecting the source and the scintillator center. Thus in electron detecting mode, the electrons are not hindered in their motion towards the scintillating plate. In ion detecting mode, the converting plates are at negative potential and attract positive ions. However a large portion of the SE from sections of the cylinders close to the ion entrance region are attracted back towards the sample, and thus the ions detection efficiency is decreased to about 50% as described in U.S. Patent Application 20040262531.

Another way to measure positive ions as disclosed in J. Krasa, M. Pfeifer, M. P. Stockli, U, Lenhert, and D. Fry, "The effect of the first dynode's geometry on the detection efficiency of 119EM electron multiplier used as a highly charged ion detector(Nucl. Instrum. And Meth. B152 (1999) 397-402) is to impinge them at typically 3 keV to 5 keV onto a converter material in the form of Venetian Blind like strips (strips at an angle to the ion motion) to produce SE.

Energetic ions can be used or the strips can be at negative voltage to accelerate slow ions towards them. The SE are attracted from the strips to an electron multiplier behind the strips. It is also shown in cited reference 5 that the efficiency to collect the SE from the strips varies from 70% to 5% depending on where the ion hit the strip.

It is generally desirable to reduce the number of detectors on any electron- or ion beam system. Multiple detectors increase system cost and occupy place in the vacuum system, which may be needed for sample manipulations. A detector capable of detecting secondary electrons, backscattered electrons and secondary ions would therefore free up space and significantly reduce manufacturing cost, provided the detector can distinguish between those particles by means of preferably automatic manipulation of voltages only, rather than mechanical adjustments or other direct operator intervention.

In view of the above, it is an object of the present invention to provide a detector with an improved selectivity and detection efficiency for secondary electrons, low energy positive ions, and tertiary electrons, originating from backscattered electrons, respectively. This object is solved by the detector according to any of the independent claims.

According to a first aspect of the invention the invention provides a particle detector for detecting secondary ions, or secondary electrons or tertiary electrons (SE3), all originating from a focused scanning ion or electron beams, said particle detector comprising:

a sparse collecting electrode; Venetian Blind strips for converting secondary ions to electrons, said Venetian Blind strips comprising a conducting material and being disposed behind the sparse collecting electrode; at least one further electrode adjacent the Venetian Blind strips, wherein said at least one further electrode enhances the detection efficiency of the particle detector; a scintillating disc for producing scintillation photons upon impingement of energetic electrons, said scintillating disc being biasable with respect to said Venetian Blind strips and said at least one further electrode, respectively; and a light-guide for guiding scintillation photons to a photo-multiplier, wherein the particle detector detects any of the type of the incoming particles, and excludes the other types by switching appropriate voltages on the electrodes.

According to a second aspect of the invention the at least one further electrode comprises a fine wire electrode in front of the Venetian Blind strips, between the Venetian Blind strips and said sparse electrode.

Said fine wire electrode preferably comprises wires extending parallel to the front edges of the Venetian Blind strips, wherein said wires may have the same pitch as the Venetian Blind strips.

A negative potential can be applied to the fine wire electrode with respect to the Venetian Blind strips in order to repel electrons originating from the Venetian Blind strips.

According to a third aspect of the invention the one further electrode comprises an extracting electrode arranged behind the Venetian Blind strip, wherein a positive potential can be applied to extracting electrode with respect to the Venetian Blind strips in order to extract electrons originating from the Venetian Blind strips.

The extracting electrode preferably comprises a fine grid or wires.

According to a fourth aspect of the invention the particle detector comprises both, the fine wire electrode and the extracting electrode.

According to a fifth aspect of the invention the particle detector has a longitudinal axis which extends from the sparse collecting electrode to the scintillating disc, and the scintillating disc is spaced apart from the Venetian Blind strips in the direction of the longitudinal axis, the detector further comprising a set of SE3 ring electrodes arranged between behind said extracting electrode.

Hence, the invention further provides a particle detector for detecting secondary ions, or secondary electrons or tertiary electrons (SE3), all originating from a focused scanning ion or electron beams, said particle detector comprising:

a sparse collecting grid electrode;

Venetian Blind strips comprising a conducting material behind the sparse collecting electrode;

a fine wire electrode in front of the Venetian Blind strips, between the Venetian Blind strips and said sparse electrode;

an extracting electrode arranged behind the Venetian Blind strip;

a set of SE3 ring electrodes arranged behind said extracting electrode;

a scintillating disc for producing light upon impingement of energetic electrons; and a light-guide for guiding the scintillation photons to a photo-multiplier, wherein the particle detector measures any of the type of the incoming particles, and excludes the other types by switching appropriate voltages on the electrodes.

The sparse collecting electrode may be tilted.

The Venetian Blind strips may be tilted at an angle between about 20 and about 30 degrees to the longitudinal axis of the detector.

The invention further provides a particle detector for detecting incoming secondary ions, or secondary electrons originating from a focused scanning ion or electron beams, said detector comprising a tilted sparse collecting electrode;

tilted Venetian Blind strips made of conducting material with high secondary emission coefficient for 3 to 5 keV ions and at 20 to 30 degrees to the detector long axis;

a fine wire electrode in front of the Venetian Blind strips;

a scintillating disc that produces light upon impingement of energetic electrons; and a light-guide to transform the scintillation photons to a photo-multiplier, wherein by switching voltages on the electrodes said detector detects secondary electrons and excludes positive ions, or detects positive ions and excludes secondary electrons.

The invention still further provides a particle detector for detecting incoming secondary electrons or tertiary electrons (SE3) that are created by back-scattered electrons, all originating from a focused scanning electron beam, said detector comprising:

a tilted sparse collecting electrode, a fine grid or wires extracting electrode a scintillating disc that produces light upon impingement of energetic electrons a set of SE3 ring electrodes between the extracting electrode and the scintillating disc a light-guide to transform the scintillation photons to a photo-multiplier, wherein by switching voltages on the electrodes detects either secondary electrons from the sample and excludes tertiary electrons created by back-scattered electrons, or by switching to other voltages detects the tertiary electrons and excludes the secondary electrons.

DETAILED DESCRIPTION OF THE INVENTION

The invention is now described with reference to the embodiments shown in the drawings which show:

FIG. 1: a schematic view of ETD detector (prior art).

Figure 2:
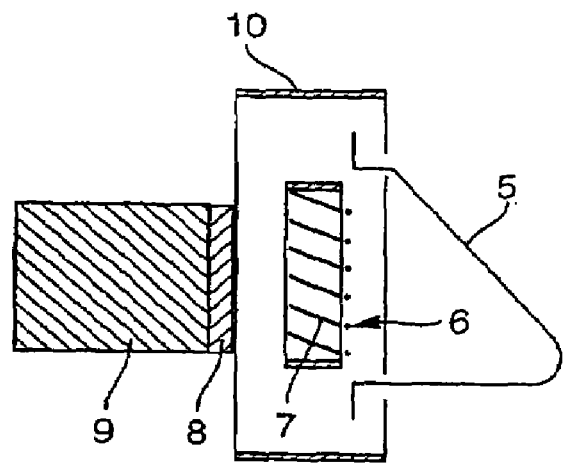
Figure 3:
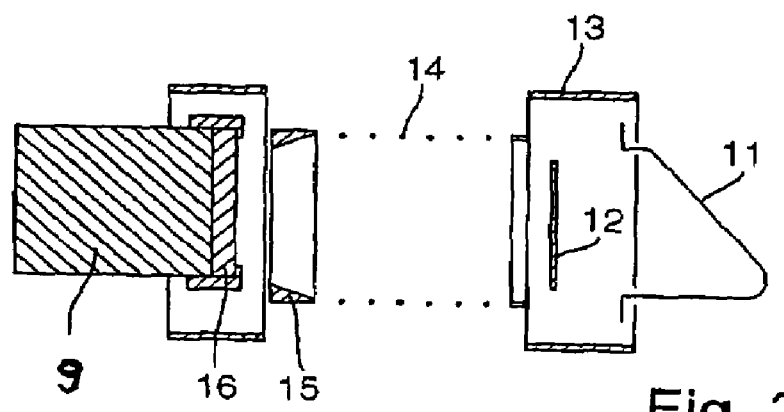
Figure 4:
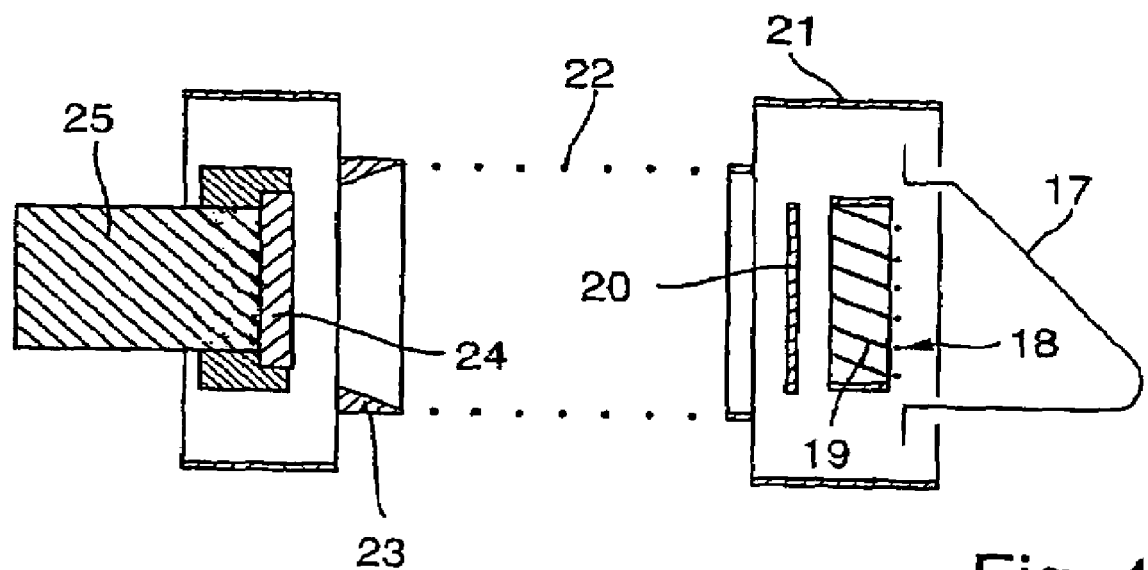

FIG. 2: a schematic cross section of low energy electrons or low energy ions detector FIG. 3: a cross section of a direct SE and SE3 detector for electron beam systems such as SEM FIG. 4: a cross section of EISE3 detector with options determined by electrode voltages to measure: Secondary electrons, or low energy secondary ions, or SE3 generated by BSE that hit various parts of the test chamber.

Figure 5:
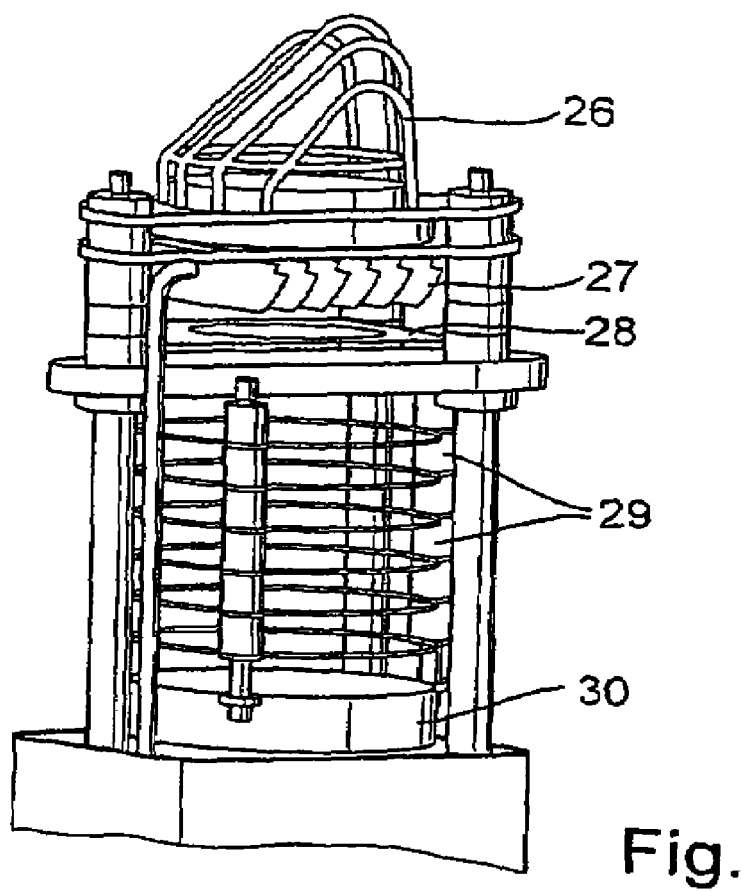

FIG. 5: an isometric side view of EISE3 detector

Figure 6:
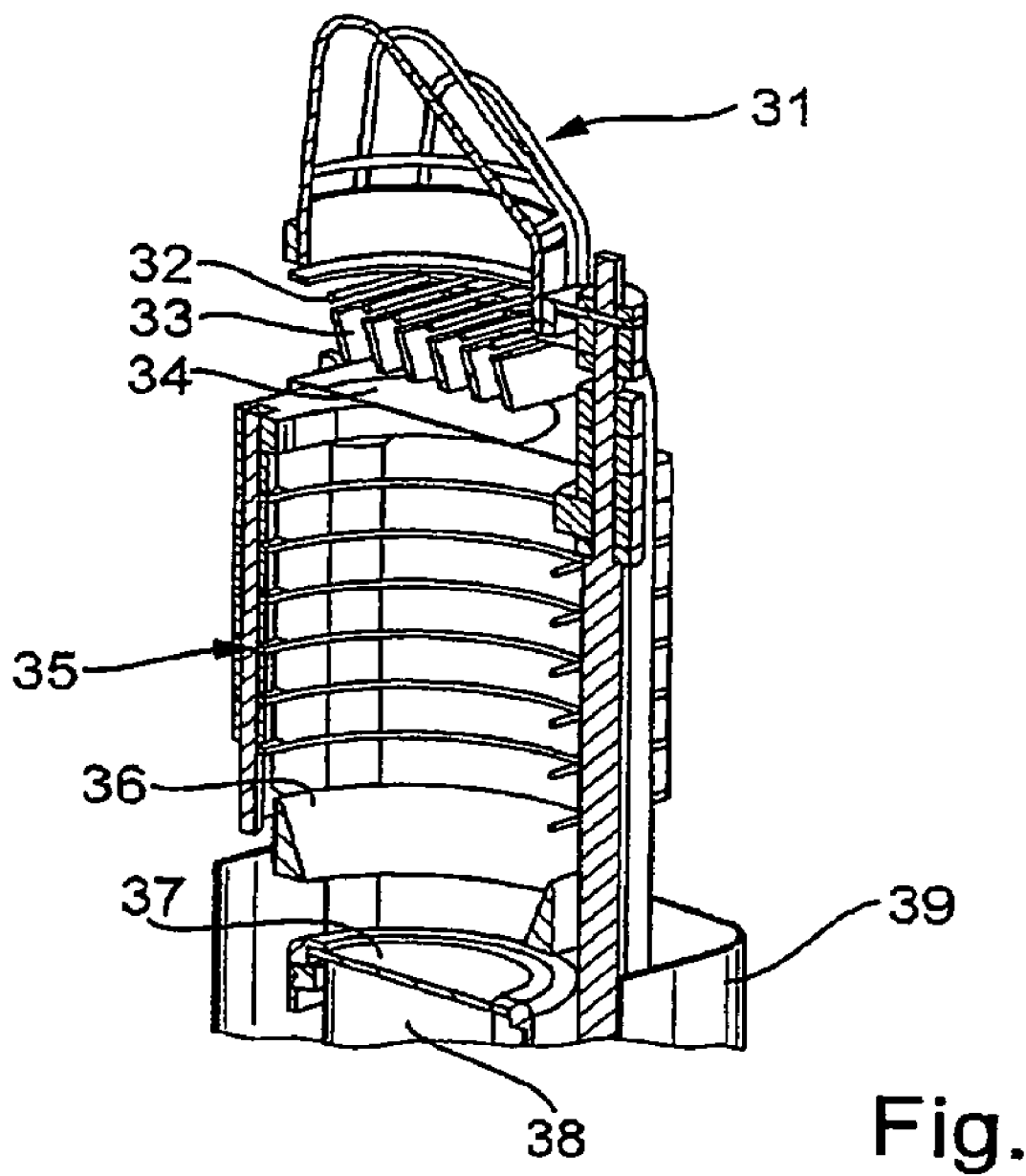

FIG. 6: one half of EISE3 detector in isometric view. The absent part is a mirror image of the shown structure.

Figure 7:
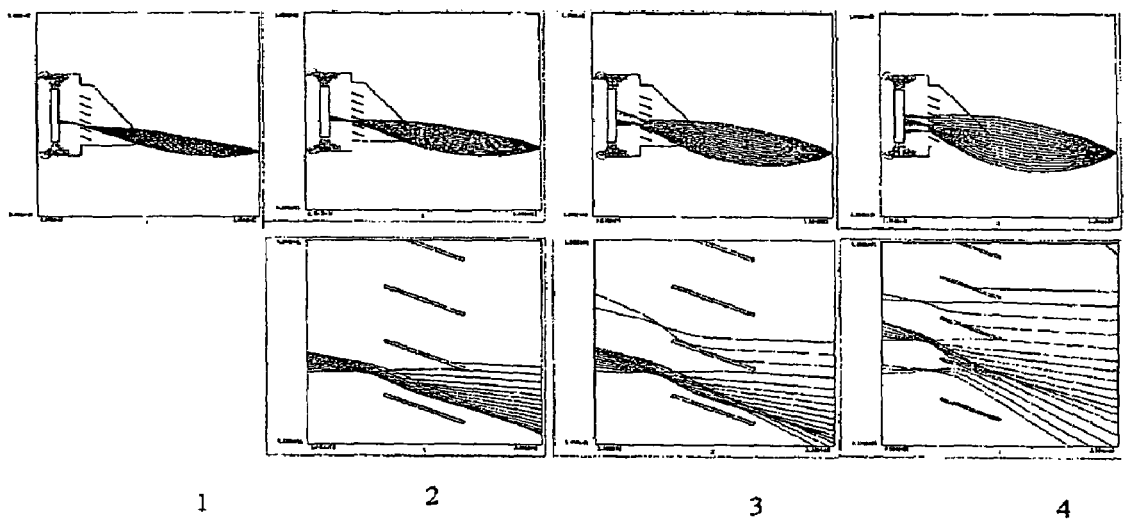

FIG. 7: simulation calculations of SE with tilted collecting sparse grid at +400 V, Venetian Blind strips at +400 V, and phosphor screen at +10 kV. The trajectories have various initial electron energies 1) −2 eV, 2) −5 eV, 3) −10 eV, 4) −20 eV. The figures in the bottom are enlargement of the trajectories in the vicinity of the Venetian Blind strips.

Figure 8:
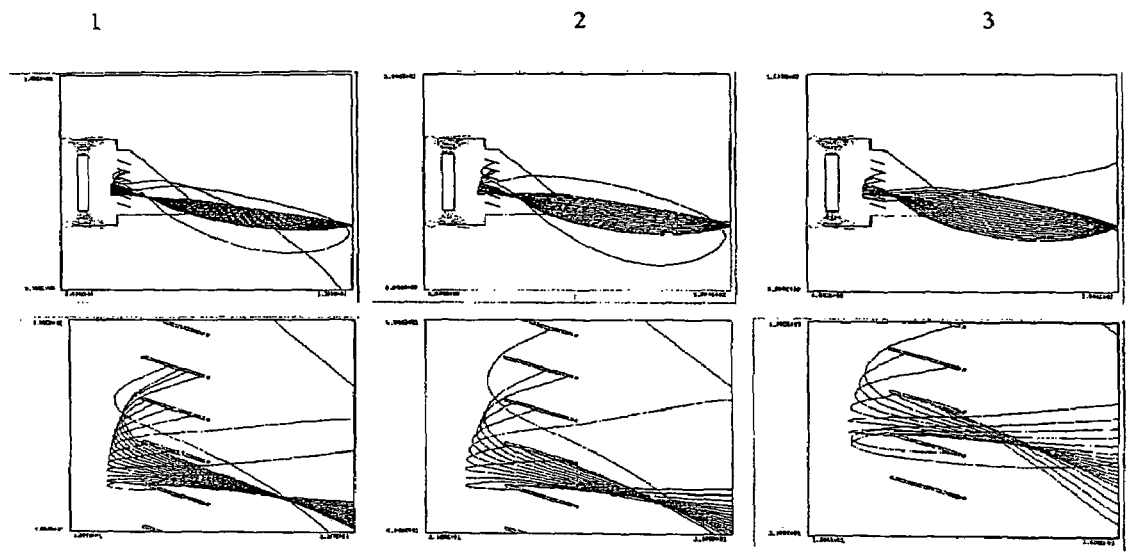

FIG. 8: trajectories of positive ions emitted from the sample at the right side of each figure, with collecting grid at −400V, fine wires (just before the Venetian Blind strips) at −3400V, Venetian Blind strips at −3000V, and Phosphor screen at +7000V. The initial energies of the ions are is: 1) −2 eV, 2) −5 eV, 3) −10 eV.

Figure 9:
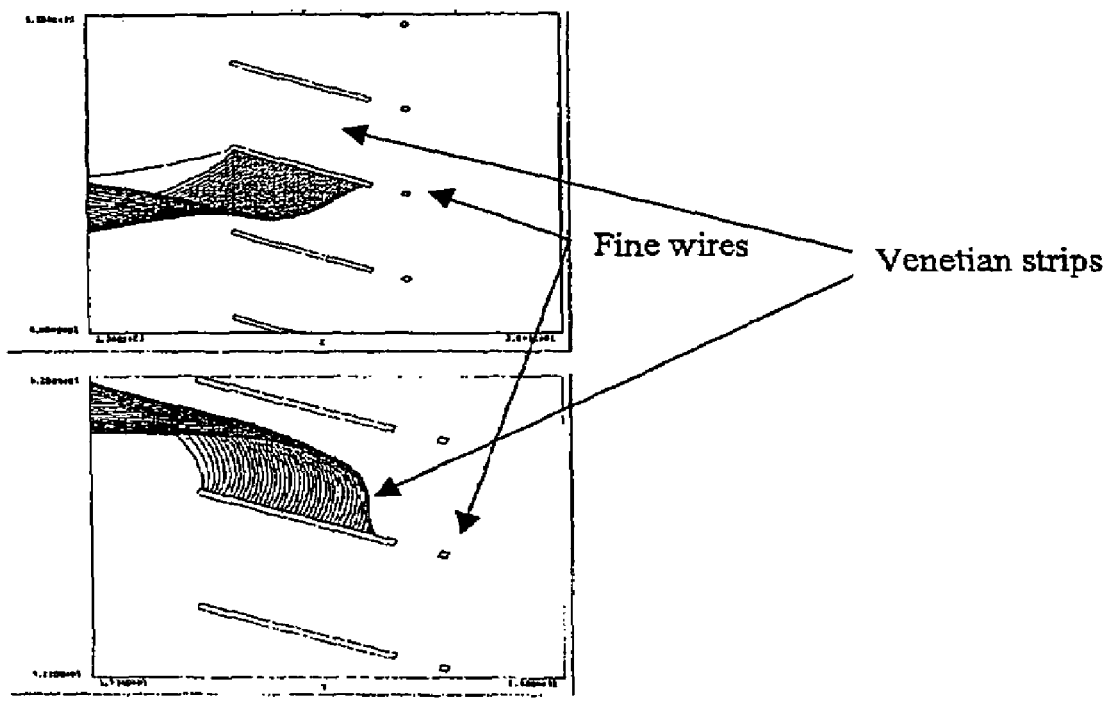

FIG. 9: a magnified view of simulation of the trajectories of ion induced SE from the Venetian Blind strips with a detector structure described in FIG. 8. The Venetian Blind strips are at −3000V and the fine wires at −3400V. The simulations assume that ion induced SE are created on the whole strip, In the two sub-figures SE are emitted once from the bottom part of the strip, and in the lower sub-figure from the top part of the strip. All the ion-induced SE are moving towards the scintillator.

Figure 10:
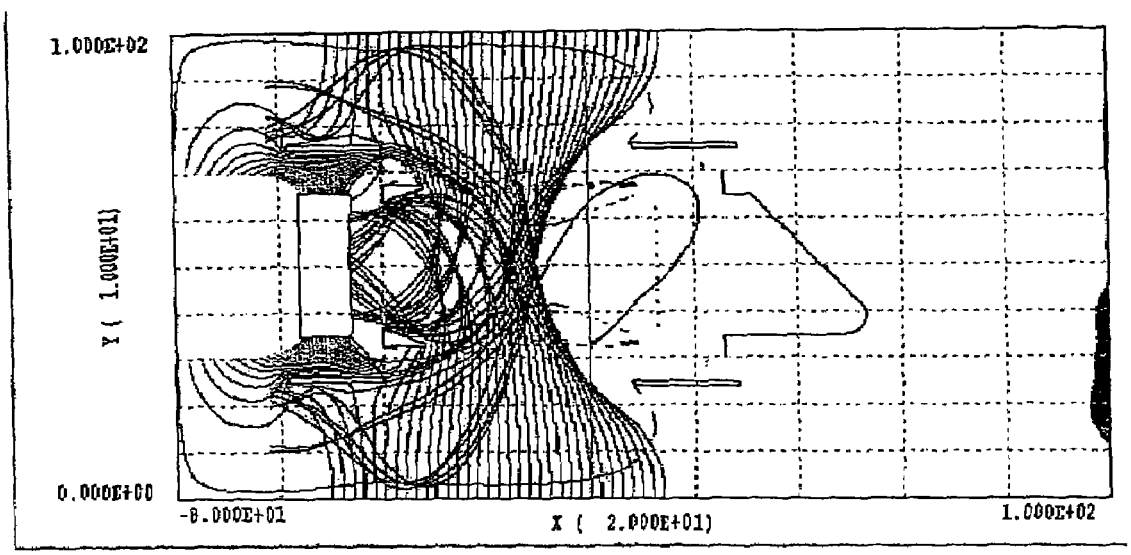

FIG. 10: a detection scheme for the detector to measure SE3 and exclude SE. Shown are trajectories of collected SE3 that were created in various parts of the chamber by BSE, and repelling electrons from the sample at the right side. The collecting tilted grid at −400V, The extracting grid is at +2.7 kV, the rings SE3 grid at +400V, and the scintillator at +10 kV.

Figure 11:
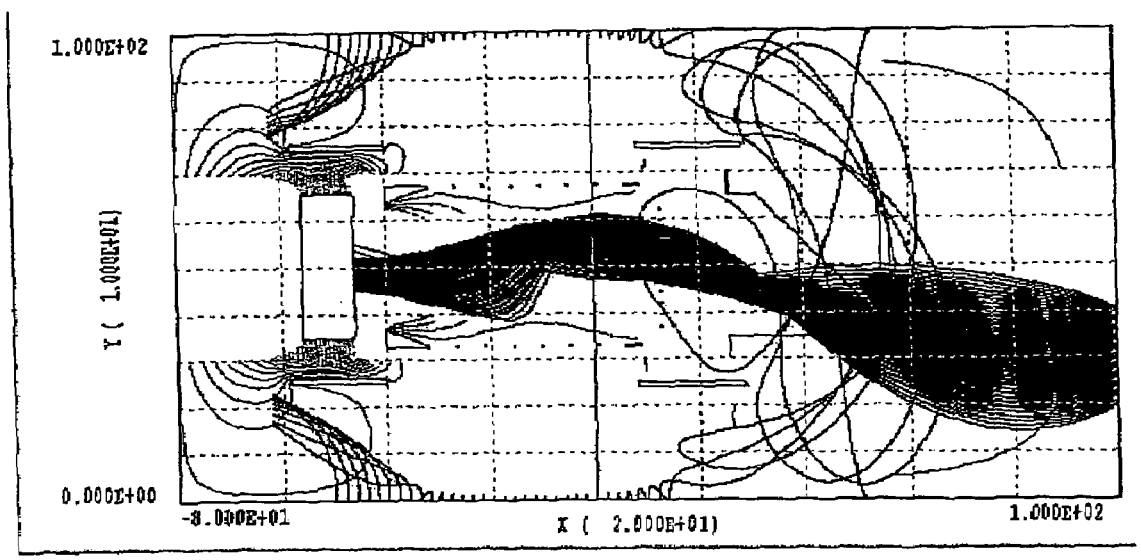

FIG. 11: a detection scheme for the detector to measure SE and exclude SE3. Shown are trajectories of from the sample and rejected SE3 that were created in various parts of the chamber by BSE. The collecting tilted grid at +400V, The extracting grid is at +2.7 kV, the rings SE3 grid at −400V, and the scintillator at +10 kV.

Two stripped down forms of the invention are described first and then combined to the basic form of the EISE3 detector.

1. The first form is an arrangement shown in FIG. 2 that can measure ions or SE by switching the voltages on the electrodes. The structure has tilted collecting sparse grid electrode 5. For ion collection the collecting sparse grid is set at low negative voltage (−80 to −500 V), fine wire electrodes 6 with a set of Venetian Blind strips 7 at voltage of −3 kV to −4 kV in front of a scintillator 8 which is at positive voltage. The SEs from the Venetian Blind strips are accelerated to the scintillator with voltage of +8 kV to +12 kV relative to the Venetian Blind strips. The fine wire electrodes 6, close to and parallel to the Venetian Blind strips in the direction of the collecting sparse grid and at several hundred Volts negative to the Venetian Blind strips, push the SE that may have been moving towards the collecting grid, towards the scintillator. In this way a high efficiency (>90%) to detect all the converted electrons is obtained. This same structure is transformed to an electron detector by just switching the voltages on the collecting grid, on the fine wire electrodes and on the Venetian Blind strips simultaneously to +100 to +500V. In the case where the positive ions from the sample or the SE from the sample originate from a very small area of less than 1×1 mm, as is the case in FIB and SEM, the Venetian Blind strips angles with respect to the sample and the voltages are designed so that in the electron detecting mode they are almost transparent to the electrons that originate from sample SEs which are accelerated towards the scintillator. Simulation calculations of SE from the sample are shown in FIG. 7. Several initial energies and initial directions are chosen to represent the whole spectrum of SE emission. The few electrons that hit the Venetian Blind strips create additional SEs which too are accelerated to the scintillator. Simulation of positive ion trajectories are shown in FIG. 8. In this figure fine wires at −400 V relative to the Venetian Blind strips repel any electron that otherwise would have been moving towards the less negative collecting grid. In a simulation of ion-induced SE from the strips shown in FIG. 9 all the SE are directed towards the scintillator. The prime novelty, over cited reference 4, is the combination of the tilted collecting grid at 20-30 degrees to the detector axis, the fine wire electrodes in front of the Venetian Blind strips, and the tilt angle of the Venetian Blind strips, that make for high efficiency (>85%) detection of either ions or electrons.

2. The second version of the detector is shown in FIG. 3. It is an SE and\or SE3 detector. There are no Venetian Blind strips for ion to electron conversion and their associated fine wires electrode. Switching voltages on the collecting and SE3 grids allow to measure one type and exclude the other. In this arrangement a scintillator 16 is placed at some 2 to 8 cm distance back. An extracting grid 12 with 2 to 4 kV voltage, in the position where the scintillator was in the first version, attracts and accelerates the SE emerging from the sample and collected by the sparse grid 11 to scintillator direction. A sparse cylindrical grid in the form of rings 14 surrounds the path to the scintillator. A low positive voltage (+100 V to +500 V) on this sparse ring grid attracts SE3 from large regions of the vacuum chamber walls and other surfaces within the chamber, while a negative potential on this grid excludes these SE3s. At the end of the SE3 grid there is a conical shaped cylindrical electrode 15 at the same voltage as the SE3 grid. It shapes the electrical field to insure that all collected SE3 or SE will hit the scintillator 16. Simulation of the trajectory of SE from the sample and SE3 from other parts of the chamber are shown in FIG. 10 and FIG. 11. It is shown that all SE reach the scintillator with SE3 rejected, or by switching voltages all SE3 reach the scintillator and SE are rejected. According to one aspect of this embodiment switching grid voltages is used to measure either SE from the sample with high efficiency and exclude SE3, or measure SE3 and exclude all direct SE, thereby allowing the generation of BSE images without using a dedicated BSE detector This version of the detector is suitable for any focused scanning e-beam device such as a SEM.

3. The EISE3 detector is a combination of the stripped down version 1 and version 2. Its schematic cross section is shown in FIG. 4. It includes a collecting sparse grid 17, a fine wire electrode 18, Venetian Blind strips 19 at an angle 20 to 30 degrees to the detector axis to allow free electron passage in SE mode, an extracting grid 20 to attract SE toward the scintillator, a cylindrical rings SE3 collecting—repelling grid 22 with a terminating ring electrode 23 having an inclined or conical inner surface at its end, a scintillating plate 24 on a light guide 25 leading to a commercial photo-multiplier (not shown). The arrangement and structure of EISE3 is shown in two isometric views in FIGS. 5 and 6. The corresponding reference numerals of FIGS. 4 through 6 are summarized in the following table:

| Feature | FIG. 4 | FIG. 5 | FIG. 6 |
|---|---|---|---|
| sparse grid | 17 | 26 | 31 |
| fine wire electrode | 18 | not shown | 32 |

-continued

| Feature | FIG. 4 | FIG. 5 | FIG. 6 |
|---|---|---|---|
| Venetian blind | 19 | 27 | 33 |
| extracting grid 20 | 20 | 28 | 34 |
| grounded body | 21 | not shown | 39 |
| SE3 collecting/repelling rings | 22 | 29 | 35 |
| terminating ring electrode | 23 | 30 | 36 |
| scintillator | 24 | not shown | 37 |
| light guide | 25 | not shown | 38 |

According to an aspect of the EISE3 detector one single structure can by just switching voltages on the grids, electrodes, and Venetian Blind strips measure or positive ions, or SE from the sample, or SE3 according to following table:

TABLE 1

Typical Voltages in V on EISE3 electrodes for selected measurements

| Detecting | Collecting sparce grid - relative to ground | Fine wires - relative to strips | Venetian Blind strips - relative to ground | Extracting grid - relative to ground | SE3 grid - relative to ground | Scintillator relative to ground |
|---|---|---|---|---|---|---|
| SE | +100 to +500 | 0 | +100 to +500 | +2000 to +4000 | −50 to −400 | +8000 to +12000 |
| Ions | −100 to −500 | −200 to −600 | −3000 to −4000 | +2000 to +4000 | −50 to −400 | +8000 to +12000 |
| SE3 | −100 to −500. | 0 | −100 to −500 | +2000 to +4000 | +100 to +500 | +8000 to +12000 |

The invention claimed is:

1. A particle detector for detecting secondary ions, or secondary electrons or tertiary electrons (SE3), all originating from a focused scanning ion and/or electron beams, said particle detector comprising:
    a sparse collecting electrode;
    Venetian Blind strips for converting secondary ions to electrons, said Venetian Blind strips comprising a conducting material and being disposed behind the sparse collecting electrode;
    at least one further electrode adjacent the Venetian Blind strips, wherein said at least one further electrode enhances the detection efficiency of the particle detector;
    a scintillating disc for producing scintillation photons upon impingement of energetic electrons, said scintillating disc being biasable with respect to said Venetian Blind strips and said at least one further electrode, respectively; and a light-guide for guiding scintillation photons to a photo-multiplier, wherein
    the particle detector detects any of the type of the incoming particles, and excludes the other types by switching appropriate voltages on the electrodes.

2. The particle detector of claim 1, wherein the at least one further electrode comprises a fine wire electrode in front of the Venetian Blind strips, between the Venetian Blind strips and said sparse electrode.

3. The particle detector of claim 2, wherein said fine wire electrode comprises wires extending parallel to the front edges of the Venetian Blind strips.

4. The particle detector of claim 3, wherein said wires have the same pitch as the Venetian Blind strips.

5. The particle detector of claim 4, wherein a negative potential can be applied to the fine wire electrode with respect to the Venetian Blind strips in order to repel electrons originating from the Venetian Blind strips.

6. The particle detector of claim 1, wherein the at least one further electrode comprises an extracting electrode arranged behind the Venetian strip, wherein a positive potential can be applied to extracting electrode with respect to the Venetian Blind strips in order to extract electrons originating from the Venetian Blind strips.

7. The particle detector of claim 6, wherein the extracting electrode comprises a fine grid or wires.

8. The particle detector according to claim 1, wherein the detector has a longitudinal axis which extends from the sparse collecting electrode to the scintillating disc, and the scintillating disc is spaced apart from the Venetian Blind strips in the direction of the longitudinal axis, the detector further comprising a set of SE3 ring electrodes arranged between behind said extracting electrode.

9. A particle detector for detecting secondary ions, or secondary electrons or tertiary electrons (SE3), all originating from a focused scanning ion and/or electron beams, said particle detector comprising:
    a sparse collecting electrode;
    Venetian Blind strips comprising a conducting material behind the sparse collecting electrode;
    a fine wire electrode in front of the Venetian Blind strips, between the Venetian Blind strips and said sparse electrode;
    an extracting electrode arranged behind the Venetian strip;
    a set of SE3 ring electrodes arranged behind said extracting electrode;
    a scintillating disc for producing light upon impingement of energetic electrons; and
    a light-guide for guiding the scintillation photons to a photo-multiplier, wherein the particle detector measures any of the type of the incoming particles, and excludes the other types by switching appropriate voltages on the electrodes.

10. The particle detector of claim 9, wherein the particle detector has a detection efficiency of more than 80%, preferably more than 85% of the incoming secondary ions, or secondary electrons or tertiary electrons (SE3), respectively.

11. The particle detector of claim 9, wherein the sparse collecting electrode is tilted.

12. The particle detector of claim 9, wherein the Venetian Blind strips are tilted at an angle between about 20 and about 30 degrees to the longitudinal axis of the detector.

13. The particle detector of claim 12, wherein the conducting material of the Venetian Blind strips has a high secondary emission coefficient for ions with a kinetic energy of about 3 to 5 keV.

14. The particle detector of claim 9, wherein the extracting electrode comprises a fine grid or wires.

15. A particle detector for detecting incoming secondary ions, or secondary electrons originating from a focused scanning ion or electron beams, said detector comprising
   a tilted sparse collecting electrode;
   tilted Venetian Blind strips made of conducting material with high secondary emission coefficient for 3 to 5 keV ions and at 20 to 30 degrees to the detector long axis;
   a fine wire electrode in front of the Venetian Blind strips;
   a scintillating disc that produces light upon impingement of energetic electrons; and
   a light-guide to transform the scintillation photons to a photo-multiplier, wherein by switching voltages on the electrodes said detector detects secondary electrons and excludes positive ions, or detects positive ions and excludes secondary electrons.

16. A particle detector for detecting incoming secondary electrons or tertiary electrons (SE3) that are created by back-scattered electrons, all originating from a focused scanning ion or electron beams, said detector comprising:
   a tilted sparse collecting electrode,
   a fine grid or wires extracting electrode
   a scintillating disc that produces light upon impingement of energetic electrons
   a set of SE3 ring electrodes between the extracting electrode and the scintillating disc
   a light-guide to transform the scintillation photons to a photo-multiplier, wherein by switching voltages on the electrodes detects either secondary electrons from the sample and excludes tertiary electrons created by backscattered electrons, or by switching to other voltages detects the tertiary electrons and excludes the secondary electrons.

17. The detector of claim 1, wherein the detector is capable to accelerate and to transmit more than 85% of all secondary electrons from the sample to the scintillating disc at energies from 5 keV to 15 keV, and to repel ions, and tertiary electrons, when switched to a secondary electron detection mode.

18. The detector of claim 1, wherein the detector is capable to detect more than 85% of all low energy positive ions from the sample when switched to ion collecting mode.

* * * * *